US006244271B1

(12) United States Patent
Turner et al.

(10) Patent No.: US 6,244,271 B1
(45) Date of Patent: Jun. 12, 2001

(54) METHOD OF USING INFANT'S GRASP IMPEDING APPARATUS

(76) Inventors: Deborah A. Turner; Wayne D. Turner, both of 6202 E. Dixileta Dr., Cave Creek, AZ (US) 85331

( * ) Notice: Subject to any disclaimer, the term of this patent is extended or adjusted under 35 U.S.C. 154(b) by 0 days.

(21) Appl. No.: 09/460,155

(22) Filed: Dec. 13, 1999

(51) Int. Cl.[7] .................................................. A61B 19/00
(52) U.S. Cl. ........................ 128/869; 128/878; 128/879
(58) Field of Search ................................... 128/869, 877, 128/878, 879; 602/20, 21, 22

(56) References Cited

U.S. PATENT DOCUMENTS

| Re. 20,858 | 9/1938 | Moller | 128/133 |
|---|---|---|---|
| 432,798 * | 7/1890 | Hirst | 128/879 |
| 1,984,613 | 12/1934 | Moller | 128/133 |
| 2,586,608 * | 2/1952 | Bryson | 128/879 |
| 2,693,794 | 11/1954 | Neville | 128/2.05 |
| 2,698,618 * | 1/1955 | Evenstad | 128/879 |
| 2,744,526 | 5/1956 | Saylors | 128/214 |
| 3,415,244 | 12/1968 | Block | 128/133 |
| 3,476,108 | 11/1969 | Matukas | 128/133 |
| 3,724,456 | 4/1973 | Waxman | 128/133 |
| 3,736,926 | 6/1973 | Irby | 128/133 |
| 4,481,942 | 11/1984 | Duncan | 128/133 |
| 5,327,918 | 7/1994 | Stewart et al. | 132/73 |

* cited by examiner

Primary Examiner—Michael A. Brown

(57) ABSTRACT

A method of using a grasp-impeding apparatus that prevents newborns from dislodging health care devices such as monitoring lines, I.V./intraarterial lines, chest tubes, endotrachael tubes, feeding tubes, central lines, and catheter tubes. The grasp-impeding apparatus is worn on the infant's hand and impedes the infant's ability to grasp components of the health care devices, and accordingly, pull and remove the health care devices. The apparatus can further be used to provide support to the palm, thereby stabilizing the hand in which the I.V. is introduced.

3 Claims, 4 Drawing Sheets

METHOD OF USING INFANT'S GRASP IMPEDING APPARATUS

FIELD OF THE INVENTION

The present invention relates to the field of neonatal heath care procedures and devices in that field to facilitate neonatal health care.

BACKGROUND

Newborns often require specialized health care. For instance, it is common in neonatal care wards to use intravenous ("I.V.") or intraarterial delivery methods to ensure that a sufficient quantity of nourishment or medicines are delivered to the infant. In fact, I.V./intraarterial delivery methods have been successfully incorporated into the accepted care procedures for most hospitals engaged in neonatal care. Equally common are catheter tubes or other monitoring equipment, some with accompanying sensors that are attached to the infant's skin via wires or leads.

Since introducing a neonatal I.V./intraarterial needle, or catheter into an infant is a sensitive procedure that can be traumatic for the infant and the infant's family that happens to be observing the procedure, it is important that an inserted I.V./intraarterial needle or catheter tube remain properly attached once it is correctly introduced into the infant. Properly attached I.V./intraarterial tubing ensures that the administered nourishment or medicine is continuously passed into the infant's veins or arteries. Similarly, a properly attached catheter tube ensures that the infant's waste is properly disposed of and accurately monitored as is sometimes necessary.

If the I.V./intraarterial catheter is dislodged from an infant, it will need to be reintroduced. The I.V./intraarterial catheter tube reintroduction procedure presents a substantial chance that the infant will be traumatized by the discomfort and increases the risk of infection. Moreover, the visual manifestations of the infant's trauma can also be traumatic to the infant's parents and hospital staff.

It is also common to monitor an infant's vital signs using monitoring equipment. The monitoring equipment is often coupled to the infant via wire leads and monitoring sensors that are attached to the infant's skin and provide feedback to the monitoring equipment or intravascular monitoring devices. The monitoring equipment is programmed to alert the hospital staff of abnormalities in the infant's vital signs who will in turn respond with an appropriate health care action and/or procedure. Such actions and/or procedures can often include several members of the hospital staff and require additional costly supplies and therefore be, accordingly, expensive.

One vital sign abnormality that requires an immediate response is an interruption of monitored vital sign input. And regardless of whether the interruption of monitoring is a result of either a health care emergency that requires a particular emergency health care procedure, or is a result of a dislodging of the monitoring sensors, the interruption of monitoring input requires an immediate response and action.

Commonly, it is the infants that tend to grasp and dislodge the, infusion lines, endotrachael tubes, I.V. needles, catheter tubes, or lead wires for monitoring equipment that is in contact with their body. For whatever reason, it is common for newborns to reach for, grasp, and pull on objects that are within reach of their body. Since health care devices such as I.V. tubes, Intraarterial lines, endotrachael tubes, chest tubes, feeding tubes, central lines, catheter tubes, and monitoring leads are among those objects typically within an infants reach, it is common for infants to grasp the tubes or leads of these health care devices. Often times, the pulling force from the infant is sufficient to either cause the complete removal of the I.V. needle, intraarterial catheter, or monitoring leads. Since the complete withdrawal or disorientation of an infant's health care device can be a health risk or at least undesirable, it would be advantageous to reduce the probability that an infant will grasp and remove the lines, tubes, or leads of their health care devices.

Previous inventions, such as disclosed in U.S. Pat. No. 2,693,794 issued to Neville, U.S. Pat. No. 2,744,526 issued to Saylors, and U.S. Pat. No. 4,481,942 issued to Duncan, disclose restraints that can be used to prevent infants from harming themselves. Restraints are, however, considered by some parents to be overly harsh, require a strict adherence to hospital policy and procedure for use, and are therefore used as a last resort for preventing a infant from indirectly causing harm to themselves. Moreover, restraints such as those disclosed in these patents would not completely immobilize the infants arms and could actually augment the likelihood that an infant swinging his arms might dislodge a tube or line of an attached health care device. Finally, the present inventions would be relatively expensive compared to the apparatus proposed for use with the present invention.

Other devices, such as those in U.S. Pat. No. 3,415,244, U.S. Pat. No. Re. 20,858, U.S. Pat. No. 1,984,613, and U.S. Pat. No. 3,476,108, completely encloses the hand. While these inventions can be useful for preventing an infant from grasping and removing the tubes or lines of their health care devices, these inventions block the infant's ability to touch and feel with their fingers thereby preventing any tactile exploration of their environment. Moreover, because these devices completely enclose the infant's hands, visual and tactile circulation assessment is not possible with the devices disclosed in these patents. Finally, some parents might consider such restraining devices an overly harsh manner of preventing infant's from harming themselves.

Finally, inventions in U.S. Pat. No. 3,736,926, U.S. Pat. No. 3,724,456, and U.S. Pat. No. 5,327,918 each discloses structures that occupy the palm area of a wearer. However, none of these devices disclose, or remotely suggest, using the inventions therein to perform the method of the present invention.

Thus, it would be beneficial to have a method of using an apparatus that humanely prevents infants from grasping and removing the lines or tubes of their health care devices. The present invention comprises a method of using a structure to humanely impede infants from grasping, pulling and dislodging the lines, tubes or leads of health care devices that are connected or attached to an infant's body.

SUMMARY OF THE INVENTION

The present invention is useful for humanely preventing infants from grasping and removing health care devices such as I.V./intraarterial lines, chest tubes, endotrachael tubes, feeding tubes, central lines, or catheter tubes and monitoring lead lines that have been introduced or attached to the infant's body. The invention comprises a method of using a grasp-impeding apparatus that has a palm-pad and a strap coupled to the palm-pad that retains the palm-pad in the palm of the infant. The palm-pad provides sufficient resistance to the infant such that a infant's hand cannot fully form a grasping fist.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DESCRIPTION OF PREFERRED EMBODIMENTS

The present invention, is a method of using a grasp-impeding apparatus 1 to prevent newborns from dislodging health care devices such as monitoring leads, I.V./intraarterial needles, and catheter tubes. The grasp-impeding apparatus 1, which is worn on the infant's hand, impedes the infant's ability to grasp components of the health care devices, and accordingly, pull and remove the health care devices.

Figure 1A:
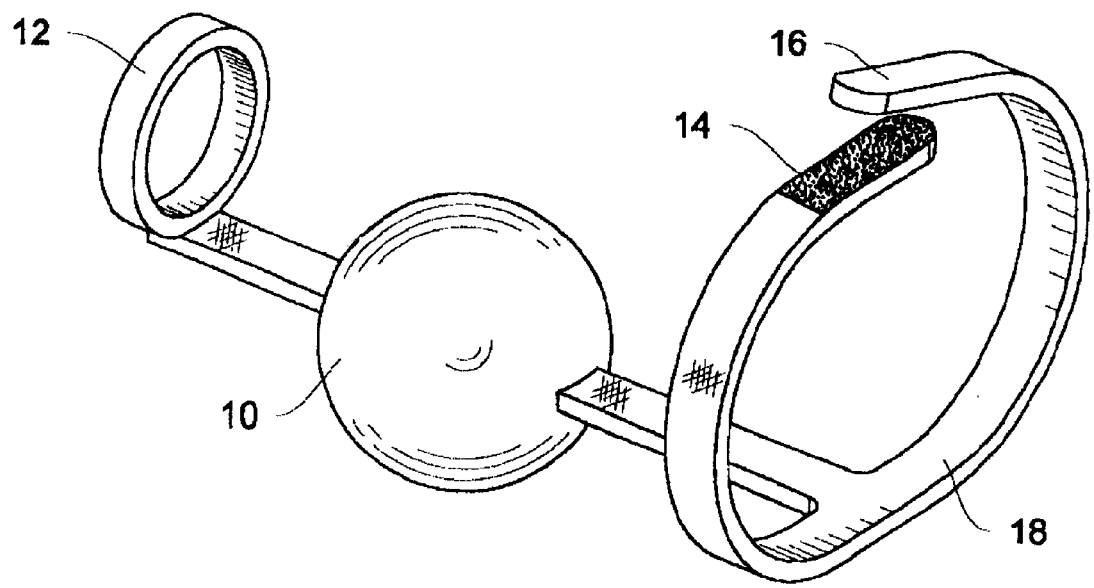
FIG. 1a depicts a perspective view of a first apparatus to be used with the present invention.
Figure 1B:
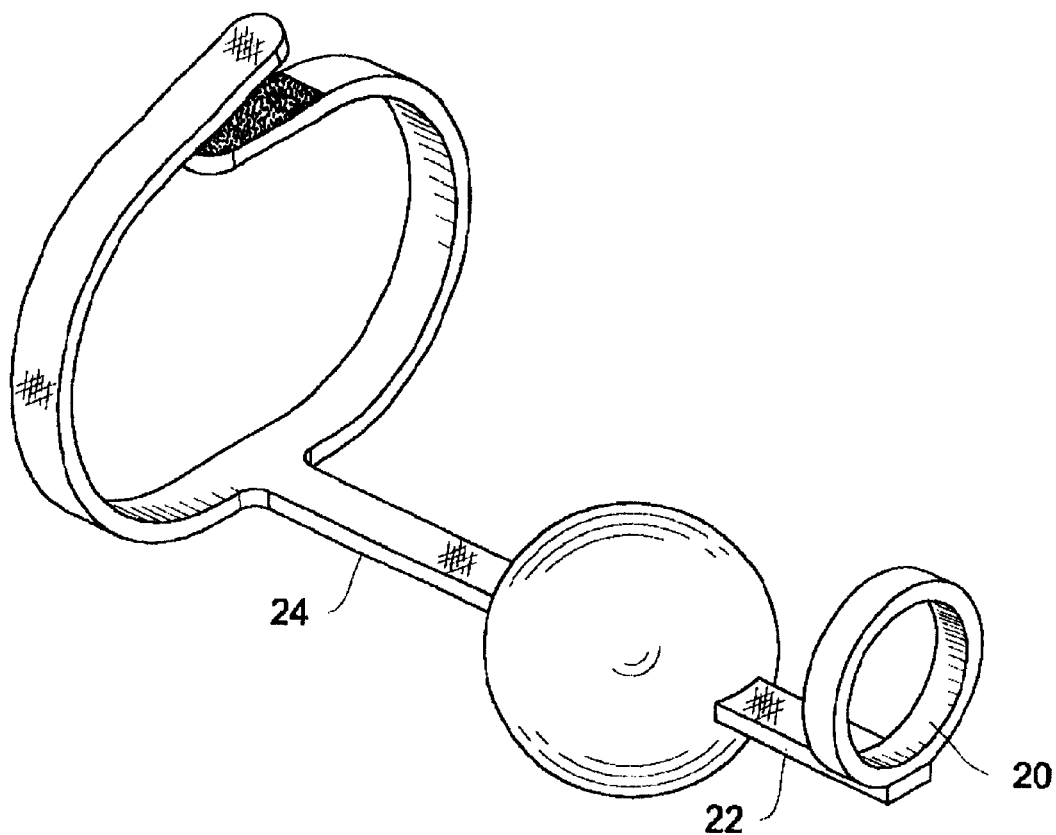
FIG. 1b depicts a reverse perspective view of the first apparatus to be used with the present invention.
Figure 1C:
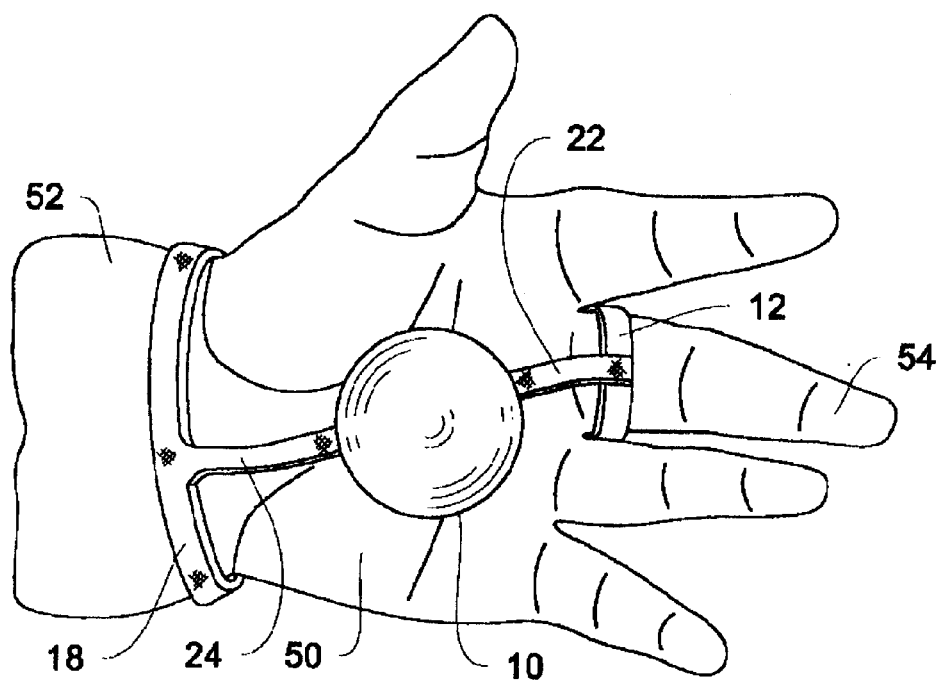
FIG. 1c & 1d depict the present invention.
Figure 1D:
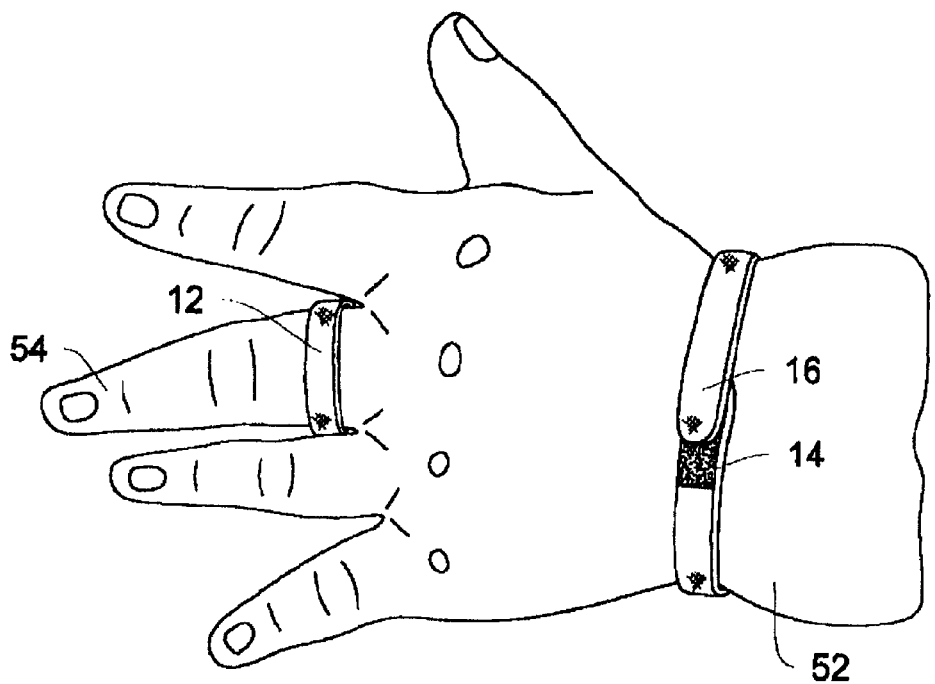
Figure 2A:
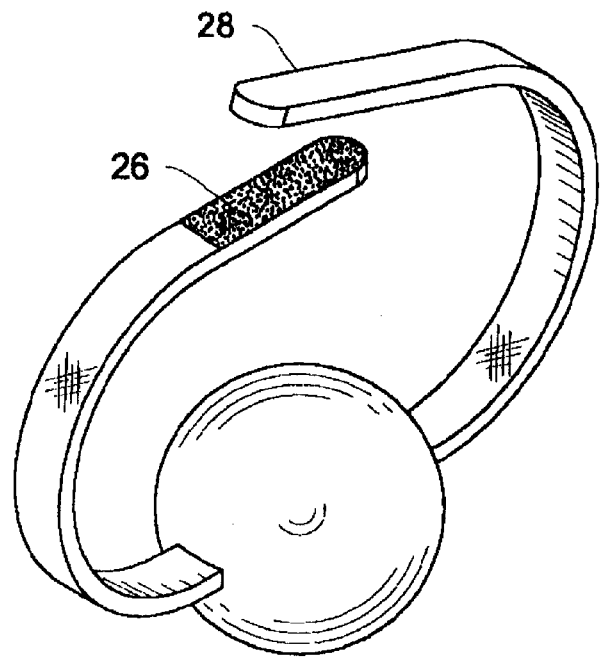
FIG. 2a & 2b depicts a second apparatus to be used with the present invention.
Figure 2B:
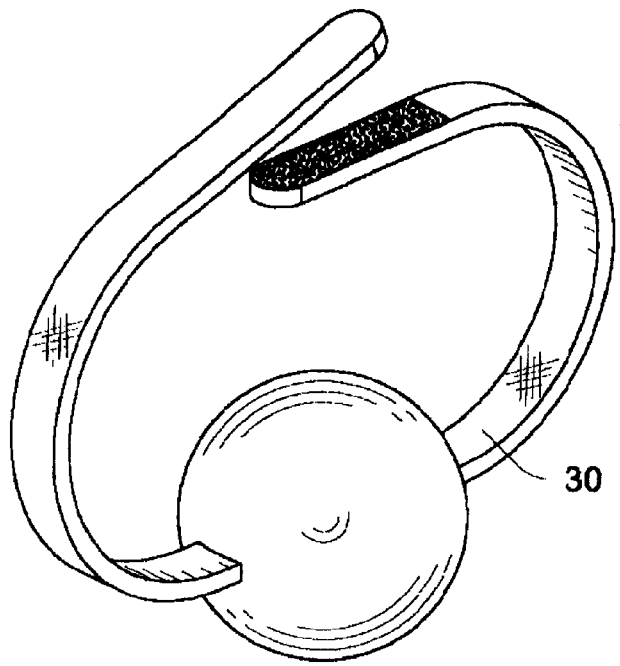
Figure 2C:
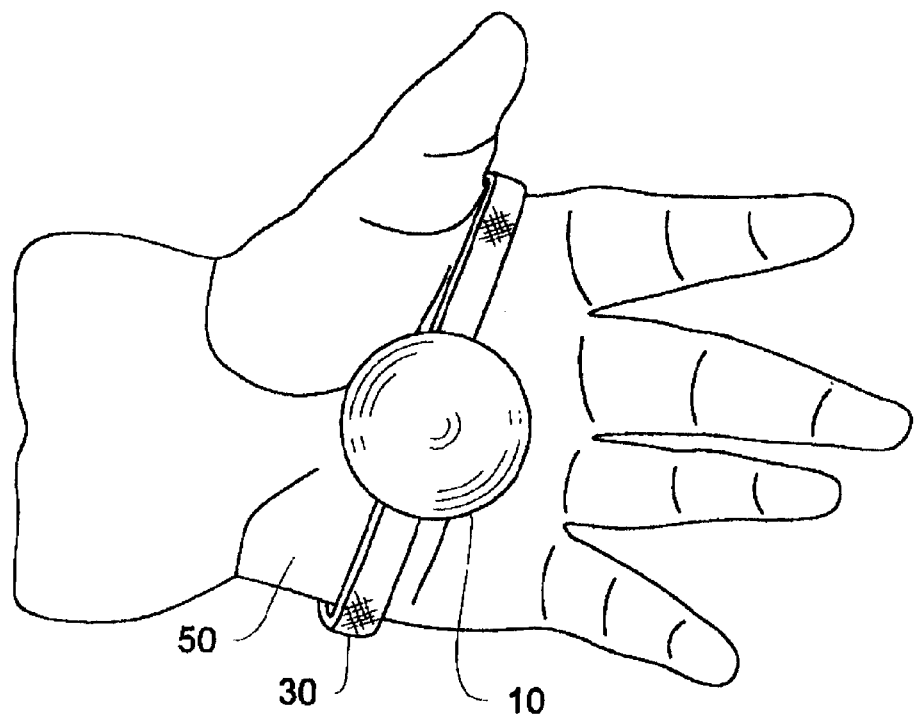
FIG. 2c & 2d depict the present invention.
Figure 2D:
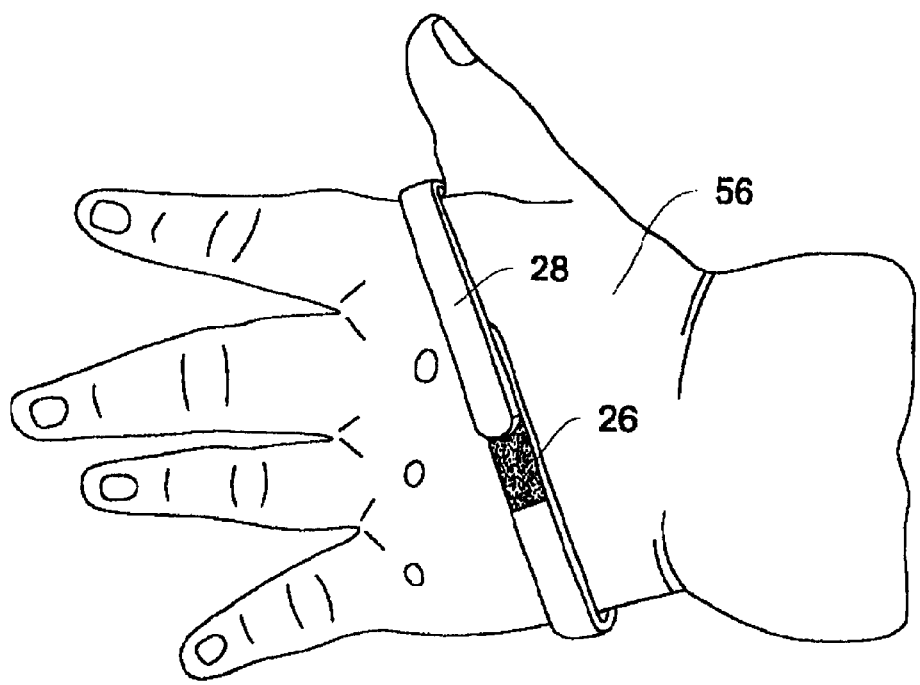

The grasp-impeding apparatus 1 most generally comprises a palm-pad 10 coupled to a strap 30. The palm-pad 10 is a structure that substantially occupies the surface area of an infant's palm and that impedes said infant from completely forming a fist. See FIG. 1c. The specific size and shape of the palm-pad 10 are non-critical, but it is contemplated that an able palm-pad 10 size would be on the order of 0.5 inches to 3 inches across at the narrowest dimension. The preferred shape of the palm-pad 10 is curved for ergonomic reasons. Particularly, the preferred palm-pad 10 shapes are substantially spherical, oval or even spoon-shaped. Alternate palm-pad 10 shapes that are also useable include cylinders, rectangles, or a shape that mirrors the shape of an infant's palm and that has ridges adapted to receive the infant's fingers. In light of the disclosed structures and the purpose of the palm-pad 10, it is contemplated that an ordinarily skilled practitioner would be capable of conceiving of many alternate structures that could function as the palm-pad 10.

Since the palm-pad 10 provides resistance to the infant's attempt to form a grasping-fist, the preferred palm-pad 10 is semi-rigid relative to the strength of an infant's grasp. The exact rigidity is not critical. Fibrous or lattice structures are able structures due to their resiliency. Alternatively, substantially rigid non-giving structures could also be used even though such structures are likely to be less comfortable than semi-rigid structures. Alternate materials are also useful for the palm-pad 10. For example, both natural and synthetic materials are able construction materials so long as the materials are non-toxic, non-shedding and non-allergenic.

The palm-pad 10 is secured to the infants hand by the at least one strap 30 that is adapted to wrap around the backside of the infant's hand. The strap 30 is coupled to the palm-pad 10 and is preferably adjustable in length to ensure a proper fit on each infant's hand. Elastic alone, or in combination with a fastener such as hook-and-loop or snaps, are preferred for constructing the strap 30. Alternatively, non-elastic strapping can also be used so long as the palm-pad 10 can be comfortably secured to the infant's hand using the strap 30. FIG. 2 depicts a two-piece strap 30 with hook-and-loop fastener attached at distal ends, 26 and 28, of the strap 30 to secure the strap 30 around the back of the infant's hand. Like the palm-pad 10, the strap 30 material should be non-toxic, non-shedding and non-allergenic.

More elaborate strapping structures can also be used to secure the palm-pad 30 to the infant's hand. For instance, FIGS. 1a–1d, depict a strapping structure that includes a two-piece wrist-strap 18 attached by a first strap extension 24 to the palm-pad 10 and at least one finger-strap 20 attached by a second strap extension 22 to the palm-pad 10. This structure is particularly beneficial because the wrist-strap 18 and the finger-strap 20 combination substantially reduce the likelihood that the palm-pad 10 will become dislodged from, or wrongly positioned on, the infant's hand. In this embodiment, hook-and-loop fastener is attached at the distal ends of the two-piece wrist-strap 18. It is clear from the description and the purpose disclosed that an ordinarily skilled person in the art could conceive of additional or alternate strapping systems.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A method of preventing an infant from grasping health care devices, comprising the step of affixing a palm pad to a palm surface of at least one hand of said infant; said palm-pad being adapted to impede the grasp of said infant by providing sufficient resistance to prevent the infant's hand from forming a grasping fist while allowing the fingers of the infant to extend freely away from the palm-pad so that the infant is provided access to suck its fingers and health care providers are allowed complete access to all of the infant's fingernails so that medical tests and measurements involving visualization of the fingernails may be performed.

2. A method of preventing an infant from grasping health care devices comprising the steps of:

affixing a wearable structure to at least one hand of said infant;

said wearable structure being adapted to impede the grasp of said infant;

said wearable structure comprising:
a palm pad; and
at least one elastic strap, coupled to said palm pad wherein said palm-pad is retained in a palm of said infant by said at least one strap that wraps around the backside of the infant's hand.

3. A method of preventing a newborn infant from harming themselves by pulling on their health care devices, comprising the steps of:

a) providing a wearable structure comprising:
   a palm pad,
   a strapping structure including a wrist strap securable about a wrist of an infant and a strap extension extending between the wrist strap and the palm pad; and
   a finger strap defining a finger opening for receiving a finger of an infant therethrough and in mechanical connection with the palm pad at a location such that when the wrist strap is wrapped around a wrist of an infant and a finger of an infant is inserted through the finger opening, the palm pad is maintained in a palm area of the infant's hand such that the grasp of the infant is impeded;

b) positioning a finger of an infant through the finger opening defined by the finger strap;

c) positioning the palm pad onto the palm area of an infant's hand; and d) securing the wrist strap about a wrist of an infant at a location such that the palm pad is maintained in a palm area of the infant's hand such that the grasp of the infant is impeded.

* * * * *